(12) United States Patent
Bauer et al.

(10) Patent No.: US 10,295,425 B2
(45) Date of Patent: May 21, 2019

(54) TEMPERATURE-COMPENSATED PRESSURE GAUGE WITH A SWITCH OUTPUT

(71) Applicant: WIKA Alexander Wiegand SE & Co. KG, Klingenberg (DE)

(72) Inventors: Nicolas Bauer, Amorbach (DE); Thomas Heckler, Grossheubach (DE); Alexander Hein, Grosswallstadt (DE); Felix Ullrich, Faulbach (DE)

(73) Assignee: WIKA Alexander Wiegand SE & Co. KG, Klingenberg (DE)

( * ) Notice: Subject to any disclaimer, the term of this patent is extended or adjusted under 35 U.S.C. 154(b) by 130 days.

(21) Appl. No.: 15/245,663

(22) Filed: Aug. 24, 2016

(65) Prior Publication Data

US 2017/0059436 A1 Mar. 2, 2017

(30) Foreign Application Priority Data

Aug. 24, 2015 (DE) .................. 10 2015 010 826

(51) Int. Cl.
| | |
|---|---|
| *G01L 7/04* | (2006.01) |
| *G01N 9/26* | (2006.01) |
| *G08B 5/24* | (2006.01) |
| *G01D 13/24* | (2006.01) |
| *G01L 19/00* | (2006.01) |
| *G01L 19/04* | (2006.01) |
| *G01L 19/12* | (2006.01) |
| *G08B 21/18* | (2006.01) |

(52) U.S. Cl.
CPC .......... *G01L 19/0092* (2013.01); *G01D 13/24* (2013.01); *G01L 7/043* (2013.01); *G01L 19/04* (2013.01); *G01L 19/12* (2013.01); *G08B 5/24* (2013.01); *G08B 21/182* (2013.01); *G01N 9/266* (2013.01)

(58) Field of Classification Search
CPC ..... G01L 19/04; G01L 19/0092; G01L 19/12; G01L 7/043; G08B 5/24; G08B 21/182; G01N 9/266
See application file for complete search history.

(56) References Cited

U.S. PATENT DOCUMENTS

| | | | | |
|---|---|---|---|---|
| 2,540,444 A | * | 2/1951 | Harland ................ | H01H 35/36 200/1 B |
| 3,075,390 A | * | 1/1963 | Sheppard ................ | G01L 7/048 73/708 |
| 4,214,474 A | * | 7/1980 | Bleidt ................... | G01L 7/048 73/30.04 |

(Continued)

FOREIGN PATENT DOCUMENTS

| | | |
|---|---|---|
| DE | 1087714 U | 3/1960 |
| DE | 10 2008 000 318 A1 | 8/2009 |

(Continued)

*Primary Examiner* — Justin Seo
*Assistant Examiner* — John M Royston
(74) *Attorney, Agent, or Firm* — Muncy, Geissler, Olds & Lowe, P.C.

(57) ABSTRACT

A monitoring device is provided having a temperature-compensated pressure-measuring system, in which an electrical notification is output to the outside with use of a plurality of settable threshold values. Also, a high-performance switching system is provided that includes at least one monitoring device.

13 Claims, 8 Drawing Sheets

(56) References Cited

U.S. PATENT DOCUMENTS

| | | | |
|---|---|---|---|
| 6,636,155 B2 * | 10/2003 | Elizondo-Salinas | G08B 5/24 |
| | | | 116/270 |
| 7,994,772 B2 | 8/2011 | Di Marco et al. | |
| 2005/0028597 A1 * | 2/2005 | Lien | G01L 7/043 |
| | | | 73/715 |
| 2009/0314615 A1 * | 12/2009 | Christensen | H01H 3/26 |
| | | | 200/17 R |

FOREIGN PATENT DOCUMENTS

| | | |
|---|---|---|
| DE | 10 2009 046 173 A1 | 5/2011 |
| DE | 10 2011 054 462 A1 | 4/2013 |
| EP | 1 850 096 A1 | 10/2007 |

* cited by examiner

TEMPERATURE-COMPENSATED PRESSURE GAUGE WITH A SWITCH OUTPUT

This nonprovisional application claims priority under 35 U.S.C. § 119(a) to German Patent Application No. 10 2015 010 826.3, which was filed in Germany on Aug. 24, 2015, and which is herein incorporated by reference.

BACKGROUND OF THE INVENTION

Field of the Invention

The invention relates to a monitoring device for the temperature-compensated monitoring of a pressure of a gas, in particular a protective gas in a high-performance switching system. The invention relates further to a high-performance switching system comprising such a monitoring device.

Description of the Background Art

Different monitoring devices for the temperature-compensated monitoring of a pressure of a gas, in particular a protective gas in a high-performance switching system, are known in general from the prior art.

Such monitoring devices called switch pressure gauges have switch units, which have, for example, magnetic snap-action contacts, inductive switch taps, or also reed switches, whereby a magnet is then coupled to a pointer for displaying the pressure on a scale.

DE 1807714 U discloses this kind of switch pressure gauge with open contacts. A switch pressure gauge with reed contacts is known from DE 10 2009 046 173 A1.

A switch pressure gauge with variable switch points is known, furthermore, from DE 10 2008 000 318 A1.

Control devices for physical monitoring measured variables with the aid of a measuring device are also known, as they are described, for example, in EP 1850096 A1 (which corresponds to U.S. Pat. No. 7,994,772 and is incorporated herein by reference) or DE 10 2011 054 462 A1, whereby electronic taps can be controlled using programmed stored switch points.

SUMMARY OF THE INVENTION

It is therefore an object of the invention to provide a monitoring device, that is improved over the prior art, for the temperature-compensated monitoring of a gas pressure and a high-performance switching system.

In an exemplary embodiment, a monitoring device is provided for the temperature-compensated monitoring of a pressure and/or density of a gas, in particular a protective gas in a high-performance switching system, which is filled, for example, with SF6, and comprises a pressure-sensing element, which has a coupling section that is deflectable in response to a gas pressure variation. Further, the monitoring device comprises a temperature-sensing element, which has a variable length between a first and second connecting section in response to a temperature variation. Further, the monitoring device comprises a main segment, rotatable about a main axis, with an articulation section attached thereto, whereby the temperature-sensing element with its first connecting section is coupled to the coupling section of the pressure-sensing element and acts with its second connecting section together with the articulation section to influence a rotational position of the main segment about the main axis. In addition, the monitoring device comprises at least one first switching unit with a first electrical switching element, which can be actuated by a rotatable cam coupled to the main segment, and a first auxiliary segment which is rotatable about the main axis and to which the first electrical switching element is attached, such that a relative position between the cam and the first electrical switching element can be changed by changing the rotational position of the first auxiliary segment.

The monitoring device by the variable relative position between the cam, actuating the switching element, and the switching element enables in a simple manner a variable specification of a switch point of the switching element, which at specific pressures or density thresholds via electrical contacts via a switch output issues a notification to the outside that a setpoint value has been reached or exceeded. In other words, the switch point of the switching unit relative to the applied pressure at the pressure-sensing element can be changed by rotating the auxiliary segment and therefore the switching element relative to the cam of the main axis. This is also possible in particular afterwards, i.e., for example, during operation of the monitoring device as well.

In this case, cost-effective encapsulated standard switches with high achievable switching capacities can be used as switching elements, which robustly retain their switching status upon jolting and are available in many versions with highly precise switching characteristics. Reference is made in this regard to the program microswitches DK, DBx from the companies Cherry, DBx, DK, DC, or UDC and to the roller switches MZx or MNx from the company Kissling, Wildberg, or switches from the companies Omron or Saia-Burgess. It is therefore possible, in comparison with electronically controlled switching elements known from the prior art, to realize the specification of the switch point and the actual switching without supplying external energy in a purely mechanical manner and therefore very robustly and with a compact structure.

The compact structure of the switching element and the coaxial arrangement of the same relative to the main axis makes it possible furthermore to realize the monitoring device itself with particularly small dimensions. Therefore, a simple arrangement of the monitoring device on the application device, in particular on a high-performance switching system, is possible, so that the temperature compensation can occur conveniently and close to the application device.

In an embodiment of the monitoring device, the pressure-sensing element is made as a Bourdon tube, sealed on one side, with, for example, an elliptical cross section. A Bourdon tube of this kind is very reliable and cost-effective.

In an embodiment of the monitoring device, the pressure-sensing element is welded pressure-tight at bottom end to a connection adapter. The pressure-sensing element itself responds to a gas pressure variation in particular in that its free end executes a movement. A deflection produced thereby is transmitted via the coupling section, which has been welded, for example, onto a lever mechanism, and can actuate a pointer mechanism or a switch, for example, the switching element. The temperature-sensing element is intermediately coupled, however, before this actuation of the switch or pointer mechanism; the element has a variable length between the first and second connecting section in response to a temperature variation of the ambient air, the air in a housing, or the gas in the gas-insulated high-performance switching system.

In an embodiment, the temperature-sensing element is a bimetallic element which, for example, has two holes as connecting sections and is integrated by means of these into the coupling mechanism. The bimetallic element is notable for its high reliability, low wear, and low-cost availability.

For example, the temperature-sensing element is connected on one side with a main segment, rotatable about the main axis and formed as a toothed segment, to the articulation section attached thereto and on the other side to the coupling section of the pressure-sensing element.

The intermediately coupled temperature-sensing element transmits a deflection of the pressure-sensing element and rotates the main segment about the main axis, on which the main segment is anchored fixed rotationally. In particular by means of tooth engagement, the rotation of the main segment in addition optionally causes a deflection of the main pointer, mounted on the main pointer shaft, via a scale. Alternatively, the monitoring device can also be made without a pointer, however.

An embodiment of the monitoring device provides that the temperature-sensing element is a bellows element, whereby the bellows element is filled with a wax or a fluid, which acts with a change in volume in response to a temperature variation and whereby in particular an external volume, coupled pressure-tight to the bellows element, is attached to an application device, i.e., to the device to be monitored, in a gas tank, or in the area of the pressure connection of the monitoring device. The bellows element in this case is also notable for a high reliability.

In an embodiment, the monitoring device comprises a second switching unit with a second electrical switching element, which can be actuated by a rotatable cam coupled to the main segment, and a second auxiliary segment, which is rotatable about the main axis and to which the second electrical switching element is attached, such that a relative position between the cam and the second electrical switching element can be changed by changing the rotational position of the second auxiliary segment. The second switching unit by the variable relative position between the second cam, actuating the second switching element, and the second switching element enables in a simple manner a variable specification of a switch point of the second switching element, which at specific pressures or density thresholds via electrical contacts and via a switch output issues a notification to the outside that a setpoint value has been reached or exceeded. In other words, the switch point of the second switching unit relative to the applied pressure at the pressure-sensing element can be changed by rotating the second auxiliary segment and therefore the second switching element relative to the cam of the main axis.

In this regard, a low-cost encapsulated standard switch with high achievable switching capacities can also be used as the second switching element.

The arrangement of the second switching unit in conjunction with the first switching unit makes it possible that a plurality of switch points can be specified variably for the monitoring device relative to the applied pressure at the pressure-sensing element. For example, different escalation steps can be realized in this case by means of the plurality of switch points when values fall below and/or exceed the allowable pressure and/or density range, for example, first an output of a warning at the switch point of the first switching unit and then a turning off of the high-performance switching system upon a further decline or further increase in the pressure and/or density. Therefore, two switching units, operatively connected to the cam on the main axis, are attached rotatably about the center of the main axis to the auxiliary segments. The switch points of the switching units can be changed relative to the applied pressure at the pressure-sensing element by rotating the auxiliary segments and therefore the switching elements relative to the associated cam on the main axis.

According to an embodiment, the monitoring device comprises a third switching unit with a third electrical switching element, which can be actuated by a rotatable cam coupled to the main segment, and a third auxiliary segment, which is rotatable about the main axis and to which the third electrical switching element is attached, such that a relative position between the cam and the third electrical switching element can be changed by changing the rotational position of the third auxiliary segment.

The arrangement of the third switching unit in conjunction with the first and second switching unit makes it possible that three switch points can be specified variably for the monitoring device relative to the applied pressure at the pressure-sensing element. Therefore, three switching units, operatively connected to the cams on the main axis, are attached rotatably about the center of the main axis to auxiliary segments. The switch points of the switching units can be changed relative to the applied pressure at the pressure-sensing element by rotating the auxiliary segments and therefore the switching elements relative to the associated cam on the main axis. For example, different escalation steps can be realized in this case by means of the three switch points when the values fall below and/or exceed the allowable pressure and/or density range, for example, first an output of an early warning at the switch point of the first switching unit and then another warning upon a further decline or further increase in the pressure and/or density and a turning off of the high-performance switching system upon a further decline or further increase.

In an embodiment, further switching units with switching elements corresponding to the first, second, or third switching unit can be provided. Therefore, a plurality of switch points and also a plurality of escalation steps and controls can be realized in a simple and low-cost manner.

According to an embodiment, the main segment comprises teeth and engages in gearing mounted on a main pointer shaft. Rotation of the main segment in this case causes a deflection of a main pointer which is mounted on the main pointer shaft and indicates the pressure and/or density of the gas.

An embodiment of the monitoring device provides that the first auxiliary segment and optionally the second auxiliary segment and optionally the third auxiliary segment can be made to engage selectively with adjustment gearing in particular manually rotatable, so that by rotating the adjustment gearing the switch point of the first electrical switching element and/or of the second electrical switching element and/or of the third electrical switching element can be adjusted with reference to the rotational position of the corresponding cam rotatable with the main segment. This axial movability of the adjustment gearing makes it possible in an especially simple manner to actuate or set a plurality of auxiliary segments with only one adjustment gearing, as a result of which an especially compact structure of the monitoring device is achieved.

The selective engagement between the rotatable adjustment gearing and the first auxiliary segment and/or the second auxiliary segment and/or the third auxiliary segment can be effected, for example, by an axial movability of the adjustment gearing. This axial movability of the adjustment gearing makes it possible in an especially simple, robust, and reliable manner to actuate or set the auxiliary segments with only one adjustment gearing.

For example, the adjustment gearing is arranged on a further shaft which is made as a square backward or forward and can be rotated with a key.

In this regard, the shaft is accessible, e.g., from the front or back through a housing opening, which can be closed with a plug. The plug, on the one hand, enables protection from penetrating foreign substances and, on the other, an unintentional shifting of the adjustment gearing.

In an embodiment, the axial movability of the adjustment gearing occurs against a spring, so that the latter automatically returns again to its starting position when not in use.

In an embodiment, the first auxiliary segment and/or the second auxiliary segment and/or the third auxiliary segment each engage in gearing mounted on an auxiliary pointer shaft, whereby rotation of the respective auxiliary segment causes a deflection of an auxiliary pointer mounted on the respective auxiliary segment. This enables in a simple, reliable, and space-saving manner a display of pressure and/or density switch points, set using the switching units, on a scale.

According to an embodiment of the monitoring device, the main pointer shaft and the at least one auxiliary pointer shaft are arranged coaxially to one another. This makes possible, on the one hand, that the main pointer and the at least one auxiliary pointer are arranged optically on a rotation axis for a user. In an arrangement of the main pointer and of the at least one auxiliary pointer behind one another on said rotation axis, a very clear presentation of a current pressure and/or a current density of the gas and simultaneously, in comparison thereto, of the at least one switch point of the switching unit is therefore possible.

The pressure-sensing element and the associated scale of the monitoring device are designed, for example, for 0 to 1.0 MPa or −0.1 to 0.9 MPa.

The switch points of the switching units optionally can also be set permanently to 0.51 or 0.54 MPa. To this end, the auxiliary segments are configured rotationally fixed, for example, by means of extension arms in a comb by welding, gluing, brazing, or pressing together.

The high-performance switching system of the invention comprises at least one electrical switching element encapsulated in a protective gas atmosphere, whereby the protective gas atmosphere is set to an allowable pressure and/or density range. Further, the high-performance switching system comprises a monitoring device of the invention or an embodiment of the same, which is integrated into the high-performance switching system to detect the pressure and/or the density of the gas, forming the protective gas atmosphere. An exceeding and/or falling below the allowable pressure and/or density range can be output to the outside by electrical signals of at least of the first electrical switching element or in addition of the second electrical switching element and/or of the third electrical switching element of the monitoring device.

According to an embodiment of the high-performance switching system, the monitoring device emits an electrical signal when the pressure and/or density of the protective gas atmosphere approaches the top or bottom limit value of the allowable pressure and/or density range at a predefined distance. Alternatively, an alarm or a warning and/or prevention of switching processes in the high-performance switching system can be generated, when the monitoring device detects a departure from a predefined pressure and/or density range, whereby a warning signal is generated if it is detected that the pressure and/or density of the protective gas atmosphere approaches the top or bottom limit value of the allowable pressure and/or density range at a predefined distance.

Further scope of applicability of the present invention will become apparent from the detailed description given hereinafter. However, it should be understood that the detailed description and specific examples, while indicating preferred embodiments of the invention, are given by way of illustration only, since various changes, combinations and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
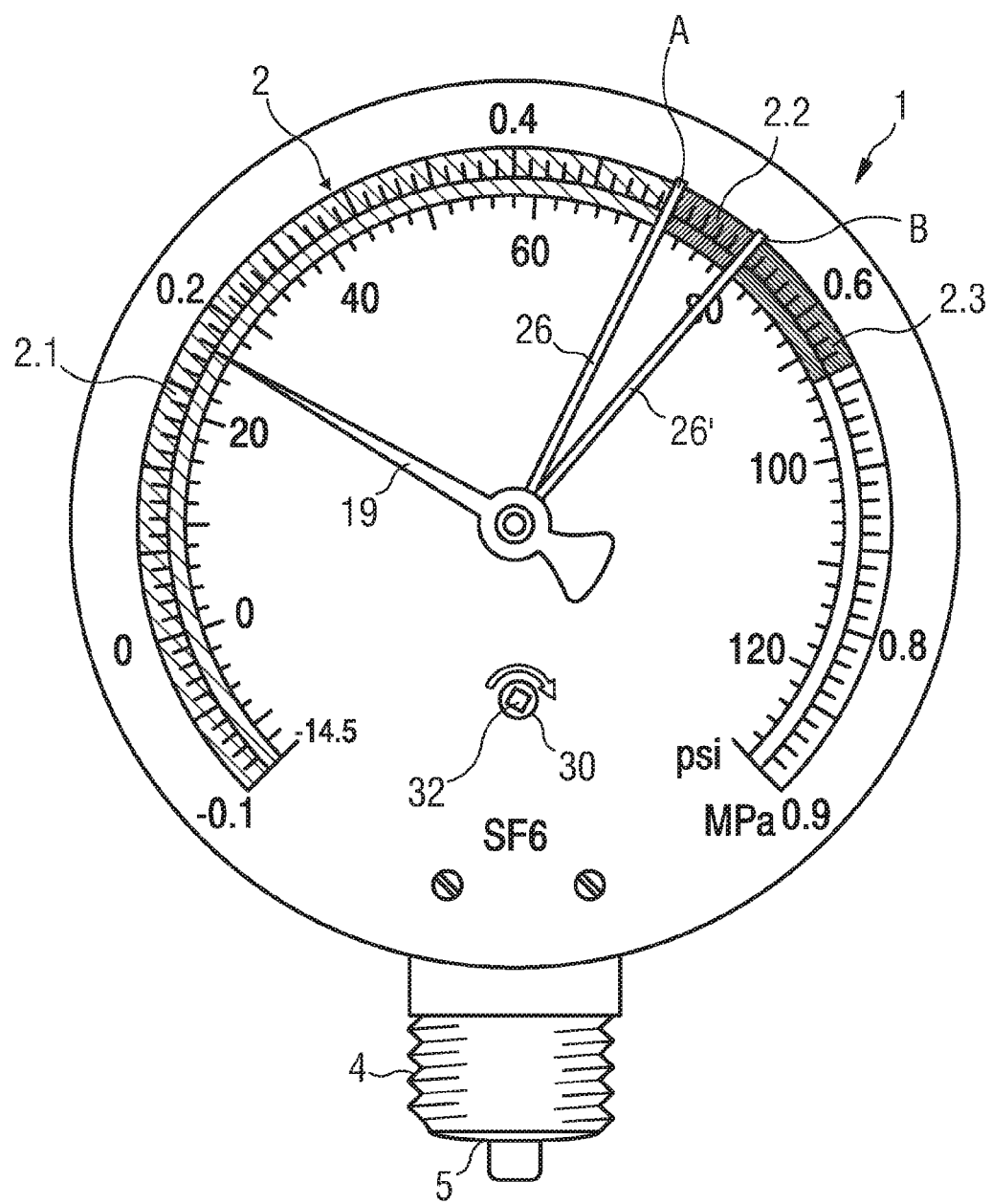
FIG. 1 shows a monitoring device from the front with a scale.

Exemplary embodiments of the invention will be illustrated hereinafter using drawings. FIG. 1 shows the monitoring device from the front with a scale.

In this case, for example, monitoring of a high-performance switching system made as a gas-insulated switching unit is designed such that monitoring device 1 has a scale 2 with a red scale section 2.1 up to a filling pressure of 85%, i.e., for example, from 0 or −0.1 MPa to 0.45 MPa (megapascal), which corresponds to a value of 74 psi.

Monitoring device 1 comprises a main pointer 19 to display the current filling pressure on scale 2.

Scale 2 can be highlighted in yellow in a second scale section 2.2 up to a second threshold value of a 90% filling pressure, therefore 78 psi or 0.47 MPa.

Scale 2 can be highlighted in green in a third scale section 2.3 above this value up to an optimal filling pressure of 92-94 psi.

The user and observer are therefore informed based on the color scheme whether and how, e.g., during filling the status or filling level of the switching unit is moving or not moving within a target range.

Furthermore, the user can now decide the positions at which he sets alarm/switching thresholds A, B. For setting said alarm/switching thresholds A, B, monitoring device 1 comprises an adjusting axis 30 with a square shaft 32, which can be operated on the front or back side of monitoring device 1 by means of a square tool (not shown) by rotation, whereby upon rotation of adjusting axis 30 the switching thresholds and simultaneously the alarm/switching thresholds A, B and auxiliary pointers 26, 26' representing said alarm/switching thresholds A, B are shifted.

For example, the user sets a first alarm threshold in the range in 0.47 MPa, which causes a refill alarm. A second threshold could be set to 0.45, whereby this could be combined with an emergency shutdown of the switching unit. It is also conceivable to integrate a second early warning threshold in a manner not shown in greater detail in this view.

Monitoring device 1 on its bottom side has a downwardly directed pressure connection 5, for example, with a thread 4. Pressure connection 5 is provided here for attachment to and for connection to the switching unit.

Figure 2:
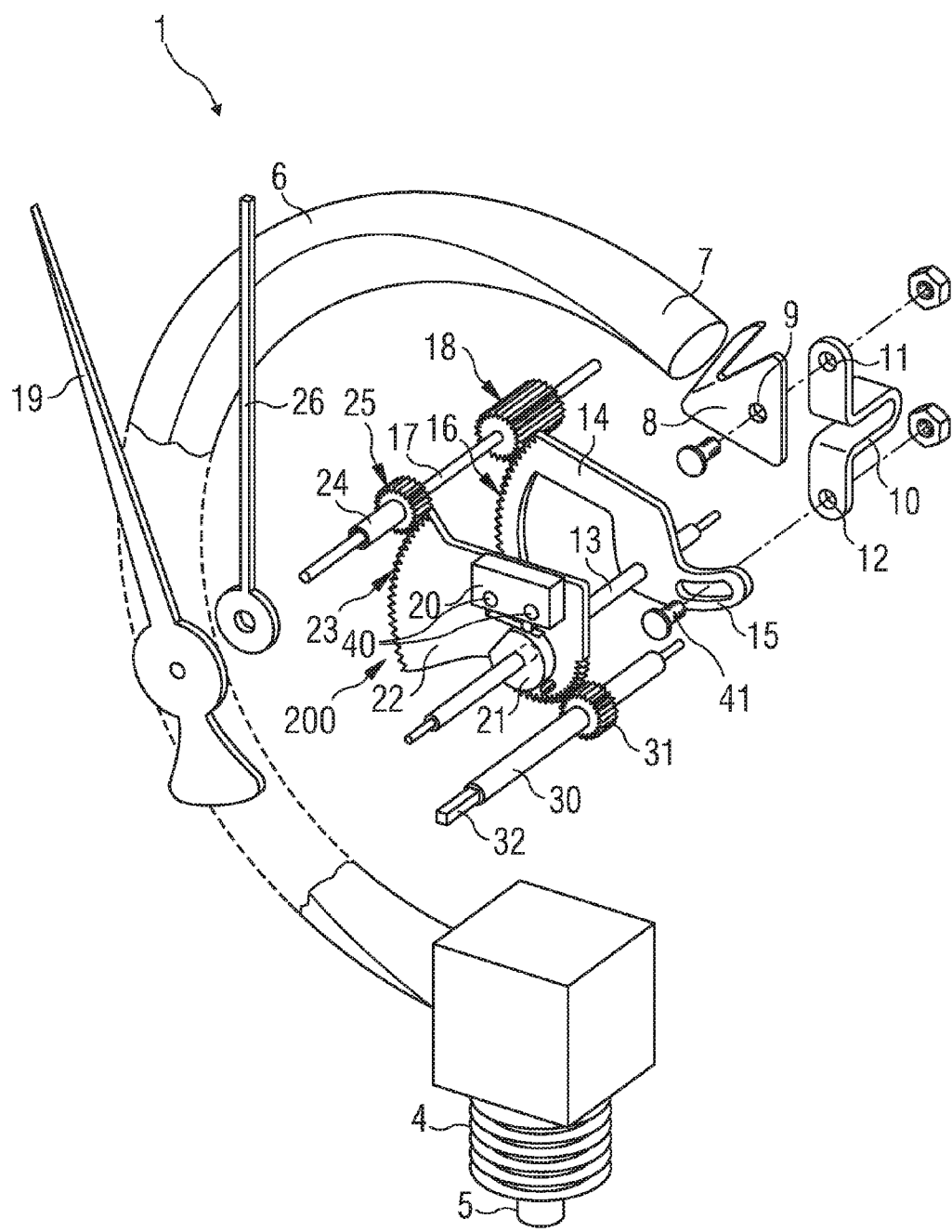
FIG. 2 shows the monitoring device in an exploded view with a switching unit and adjustable cam.

FIG. 2 shows the monitoring device in an exploded view with a switching unit and adjustable cam.

Monitoring device 1 comprises a pressure connection 5 and a pressure-sensing element 6, which is sealingly connected thereto and in the shown exemplary embodiment is a Bourdon tube with an elliptical cross section, which deflects with its free end 7 in response to a gas pressure variation at pressure connection 5.

A coupling section 8, attached to said free end 7, has a hole 9 to which a U-shaped temperature-sensing element 10 is attached rotatably.

Temperature-sensing element 10 is, for example, a bimetal and in response to a temperature variation changes a length between its two connecting sections 11, 12, formed as holes.

Temperature-sensing element 10 with its bottom connecting section 12 moves an articulation section 15 attached to a main segment 14, formed as a toothed segment rotatable about a main axis 13. To this end, temperature-sensing element 10 is coupled with its first connecting section 11 to coupling section 8 of pressure-sensing element 6 and with its second connecting section 12 to articulation section 15.

Articulation section 15 to this end is provided in particular with a long hole, so that an engaging position of temperature-sensing element 10 to articulation section 15 is variable. A lever ratio in particular to main axis 13 can be set in this way.

A rotation position of main segment 14 about main axis 13 is therefore influenced by a pressure-induced deflection of pressure-sensing element 6 and in the case of a temperature change by temperature-sensing element 10. Therefore, both a temperature-compensated pressure measurement and a density measurement or filling pressure measurement of a container can be performed by monitoring device 1, if temperature-sensing element 10 is placed as close as possible to the container to be monitored or if due to the structural proximity the temperature in the switching unit is nearly the same as in the gas of the gas-insulated switch to be monitored.

Main segment 14 with its teeth 16 is engaged with gearing 18 mounted on a main pointer shaft 17. Rotation of main segment 14 therefore causes a rotation of main pointer shaft 17 and also deflects a main pointer 19, attached to main pointer shaft 17, via a scale (not shown), for example, scale 2 shown in FIG. 1.

Further, a switching unit 200 is connected to said system, whereby a switching element 20 formed as a microswitch can be actuated by a cam 21 which is connected to main axis 13 and responds depending on the temperature-compensated internal pressure in pressure-sensing element 6.

Switching element 20 is mounted on auxiliary segment 22, rotatable about main axis 13, such that a relative position between cam 21 and electrical switching element 20 can be changed by rotating first auxiliary segment 22 about main axis 13.

Furthermore, the rotation of auxiliary segment 22 by teeth 23 causes a rotation of an auxiliary pointer shaft 24 by toothed wheel 25 mounted thereon. A rotation of the respective auxiliary segment 22 together with switching element 20 therefore causes a change in the response point for cam 21 and for the internal pressure in pressure-sensing element 6 or the closed gas container, and simultaneously causes a deflection of an auxiliary pointer 26 mounted on the respective auxiliary pointer shaft 24.

Auxiliary pointer shaft 24 is formed for this purpose as a hollow axis coaxial to main pointer shaft 17. The particular response pressure of switching element 20 is therefore displayed concurrently with the shifting of auxiliary segment 22.

To this end, however, a precise calibration and adjustment of cam 21 to main axis 13 is necessary beforehand, as is an alignment of switching unit 200 with auxiliary segment 22 and thereafter an alignment of auxiliary pointer 26 to the response pressure via scale 2.

Auxiliary segment 22 with switching element 20 seated thereon can be shifted manually by means of an adjustment axis 30, which is formed as a rotatable shaft and on which adjustment gearing 31 is mounted.

For example, rotation of adjusting axis 30 and therefore rotation of adjustment gearing 31 are effected by placing a key on the coaxially mounted square shaft 32. In this case, auxiliary segment 22 is moved together with switching element 20 and its switch point for cam 21 is changed.

An inadvertent shifting of the switch point can be prevented in that auxiliary segment 22 is pressed, for example, against another plate in a manner not illustrated in greater detail by friction or rubbing or spring elements, as a result of which a vibration-induced rotation, for example, is prevented.

In order to assure a correct and precise functioning of monitoring device 1, calibration and adjustment of the same are necessary.

To this end, in one regard, alignment of switching element 20, which is premounted, for example, on auxiliary element 22, relative to adjustment axis 30 is necessary. In a fine adjustment, switching element 20 is aligned with use of its holes 40 relative to auxiliary segment 22.

Furthermore, cam 21 on main axis 13 is aligned and connected rotationally fixed to it, whereby the rotationally fixed connection occurs frictionally, by material bonding, and/or by positive locking, for example, by means of a clamp screw or gluing.

Further, the articulation point on articulation section 15 of main segment 14 is aligned and fixed in the long hole. Articulation section 15 to this end is provided in particular with a long hole and is provided with a special screw so that the temperature-sensing element 10 can engage freely with an adjustment screw 41 without jamming. In this case, tolerances of adjustment screw 41 to the long hole and of the long hole on temperature-sensing element 10 are designed so that play is minimized.

The articulation point as well of pressure-sensing element 6, which is given by a position of hole 9 on coupling section 8 to connecting section 11, formed as a hole, of temperature-sensing element 10, is previously established in a measurement/calculation or calibration process.

Auxiliary pointer 26 is aligned with auxiliary pointer shaft 24 in its pressure matching switch point of switching element 20 at pressure connection 5 by a comparative measurement with a fine manometer or with the aid of a fine pressure regulator.

Figure 3:
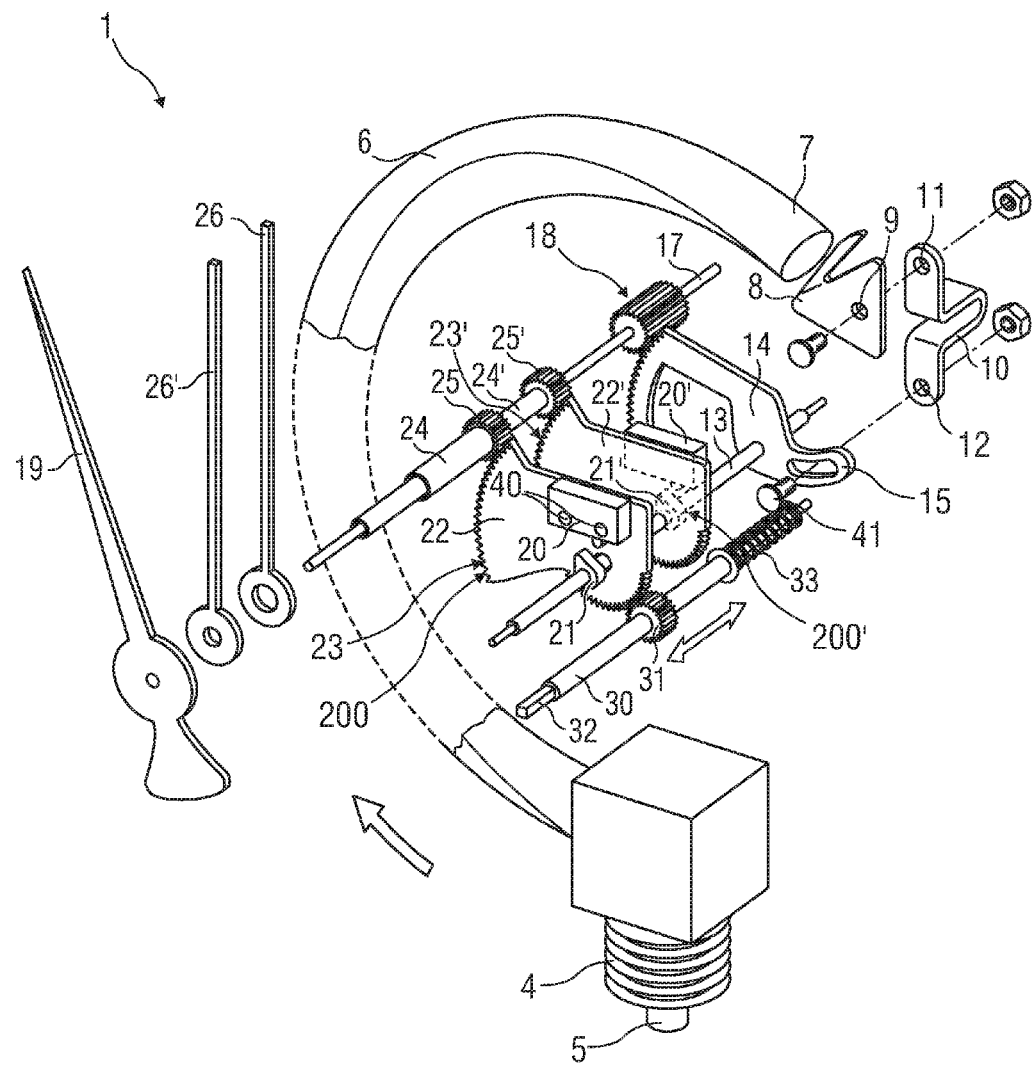
FIG. 3 shows the monitoring device in an exploded view with two switching units.

FIG. 3 shows the monitoring device in an exploded view with two switching units.

In the illustrated embodiment of monitoring device 1, in addition to the embodiment shown in FIG. 2, a further switching unit 200' is provided, which is mounted mirror-inverted to first switching unit 200.

Second switching unit 200' comprises a second switching element 20', which is likewise formed as a microswitch and which can be actuated by a second cam 21' connected to main axis 13. Second cam 21' responds to a second pressure threshold value in pressure-sensing element 6.

Switching element 20' is mounted parallel to switching element 20 and to the same main axis 13 on a rotatable second auxiliary segment 22'.

Furthermore, rotation of auxiliary segment 22' by means of affixed teeth 23', engaging with a toothed wheel 25', causes a rotation of a further coaxial, hollow auxiliary pointer shaft 24', which is mounted coaxially to further auxiliary pointer shaft 24.

Auxiliary segments 22 and 22' can be moved manually by a single rotatable adjustment axis 30, which is movable against a spring 33 and is made as a shaft, and on which an adjustment gearing 31 is mounted. Adjustment gearing 31 can be engaged selectively optionally with auxiliary segments 22, 22', for example, by sliding.

For example, rotation of the various auxiliary segments 22, 22' is made possible by placing and moving a key on the coaxially mounted square shaft 32. Because of the parallel mirror-inverted structure, this system with two switch points is characterized by a very compact design.

The calibration and adjustment of monitoring device 1 occur in analogy to the description in FIG. 2 in addition for second switching unit 200' as well.

Figure 4:
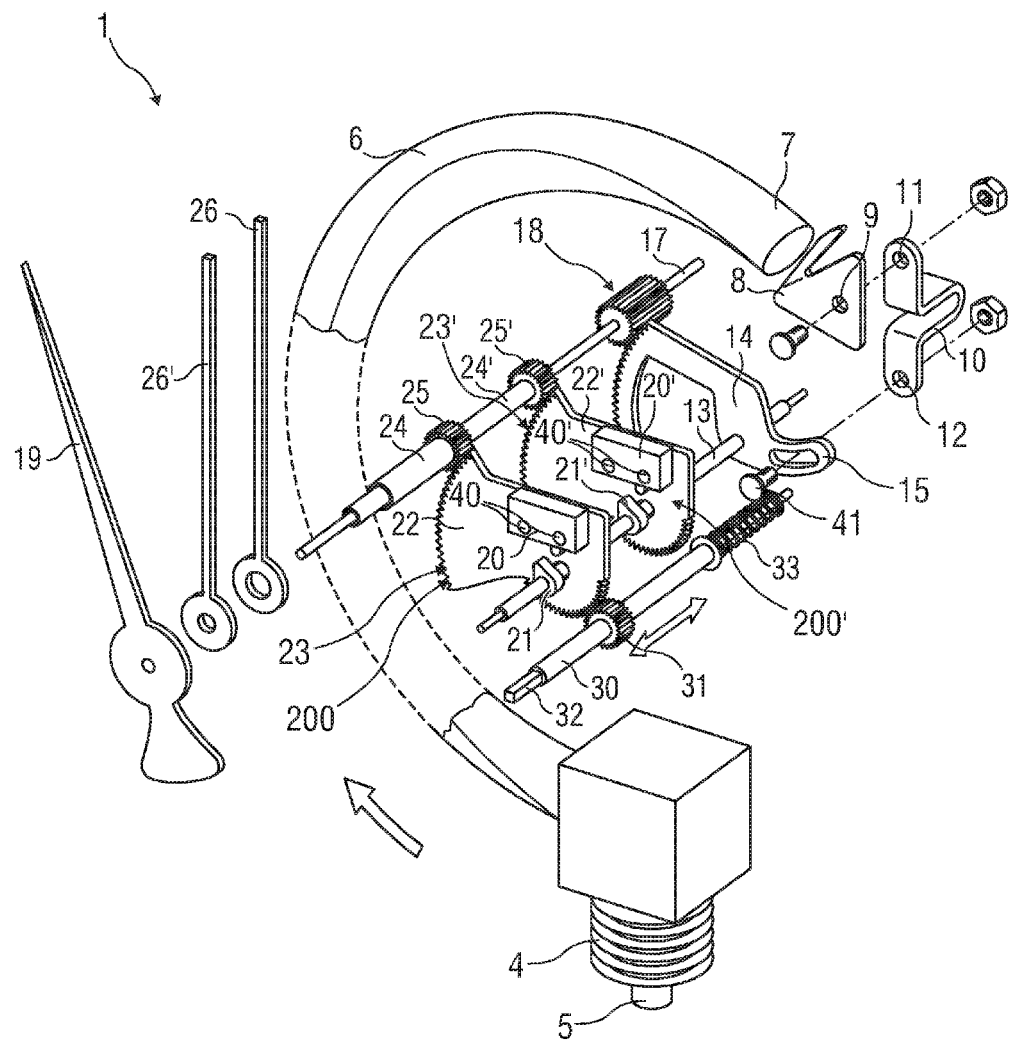
FIG. 4 shows the monitoring device in an exploded view with two identically oriented switching units.

FIG. 4 shows the monitoring device in an exploded view with two identically oriented switching units.

In contrast to the exemplary embodiment shown in FIG. 3, switching units 200, 200' with switching elements 20, 20' are oriented in the same way. Second switching element 20' also comprises holes 40', which in analogy to holes 40 of first switching element 20 can be used for calibrating and adjusting switching element 20' to auxiliary segment 22'.

The calibration and adjustment of monitoring device 1 occur in analogy to the description in FIG. 2 in addition for second switching unit 200' as well.

The illustrated structure of monitoring device 1 is especially cost-effective, because many identical parts can be used and all parts are oriented in one direction during the adjustment of switch points.

Figure 5:
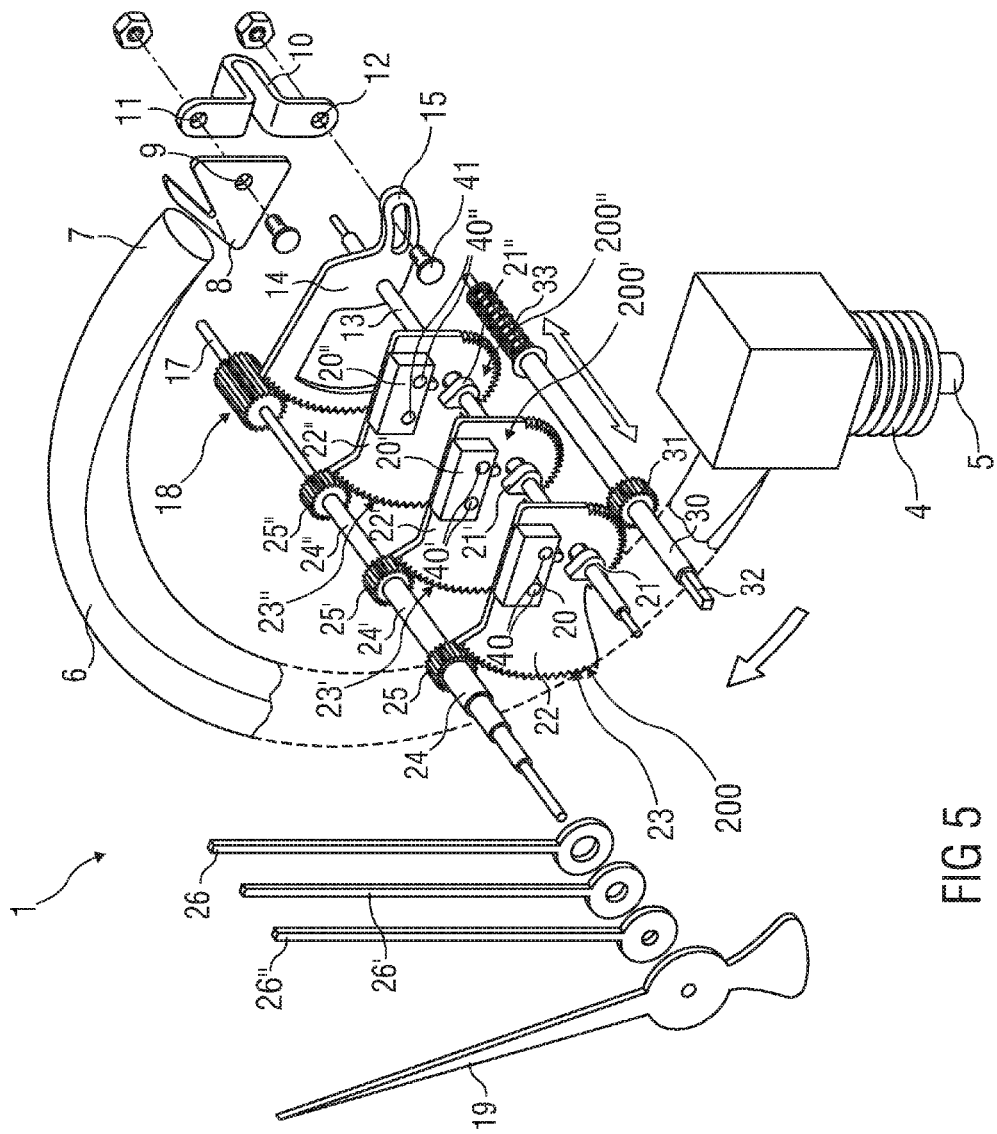
FIG. 5 shows the monitoring device in an exploded view with three identically oriented switching units.

FIG. 5 shows the monitoring device in an exploded view with three identically oriented switching units.

In contrast to the exemplary embodiment illustrated in FIG. 4, monitoring device 1 comprises in addition a third switching unit 200" with a third electrical switching element 20", which can be actuated by a rotatable cam 21" coupled to main segment 14, and a third auxiliary segment 22", which is rotatable about main axis 13 and on which third electrical switching element 20" is mounted such that a relative position between cam 21" and third electrical switching element 20" can be changed by changing the rotational position of third auxiliary segment 22".

Third switching unit 200" corresponds here in its structure in the illustrated exemplary embodiment to second switching unit 200' according to FIG. 4, whereby rotating auxiliary segment 22" by attached teeth 23", engaged with a toothed wheel 25", causes a rotation of a further coaxial, hollow auxiliary pointer shaft 24" which has an auxiliary pointer 26" and is mounted coaxially to the two further auxiliary pointer shafts 24, 24'.

Third switching element 20" also comprises holes 40", which in analogy to holes 40 of first switching element 20 can be used for calibrating and adjusting switching element 20" to auxiliary segment 22".

The calibration and adjustment of monitoring device 1 occur in analogy to the description in FIG. 2 in addition for second switching unit 200' and third switching unit 200" as well.

The illustrated structure of monitoring device 1 is of particular advantage, if different alarms are to be made possible before the actual critical falling below of a pressure and/or density level. Thus, for example, in the illustrated embodiment, a first alarm threshold in the still very non-critical range can easily have the result that a service technician checks this system only during a next service visit and optionally refills it, and therefore no "alarm callout" occurs.

An additional initial notification of this type or a threshold also called a "third contact/pressure level" is not called an alarm threshold for this reason but a "service threshold."

Figure 6:
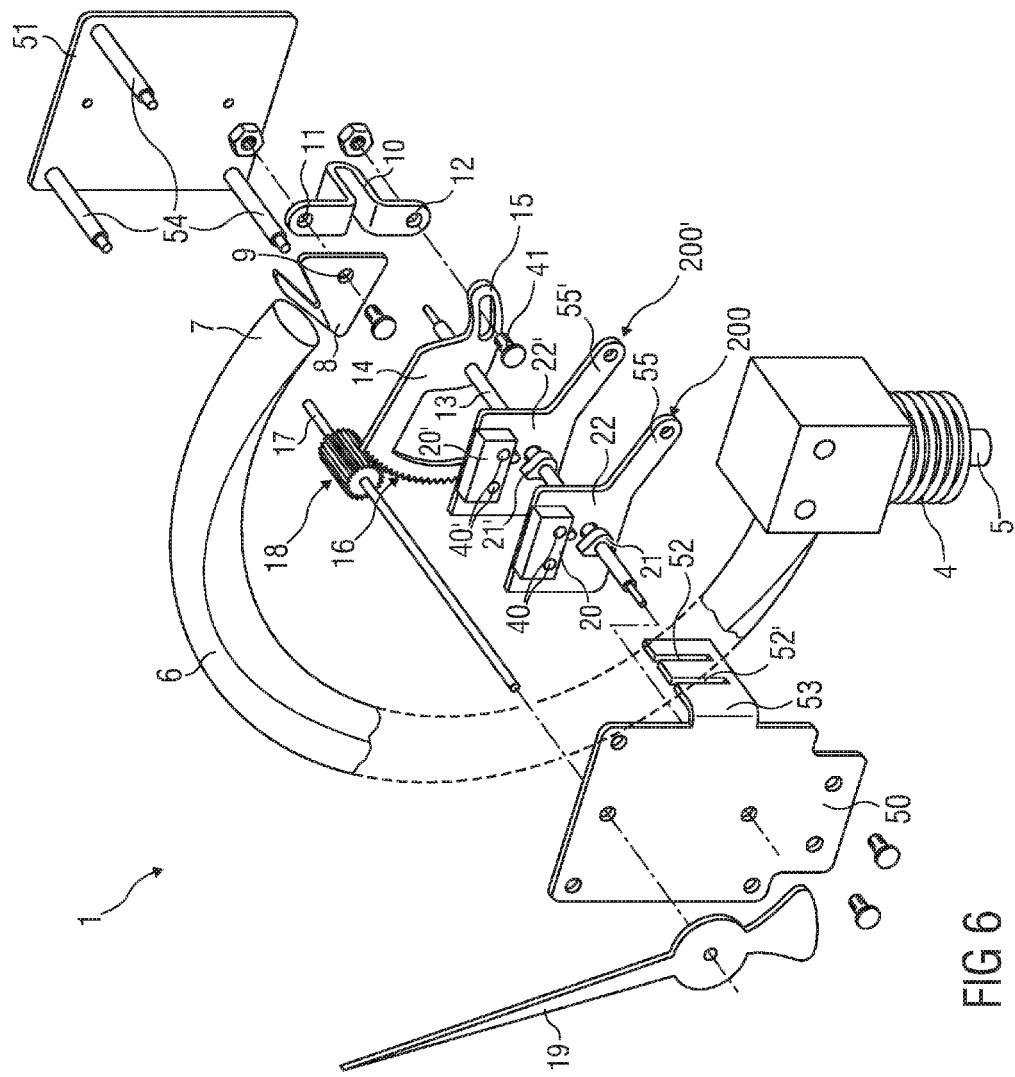
FIG. 6 shows the monitoring device in an exploded view with two identically oriented switching units, which are fixable, and with a front and rear baseplate.

FIG. 6 shows the monitoring device in an exploded view with two identically oriented switching units, which are fixable, and with a front and rear baseplate.

In the illustrated exemplary embodiment of monitoring device 1, a front baseplate 50 is connected to a rear baseplate 51, for example, by three stud bolts 54, which can be connected by screws or by stamping with front baseplate 50.

Auxiliary segments 22, 22' comprise integrally formed fastening arms 55, 55', which for setting and fine adjustment engage in slots 52, 52', which in turn are realized in a section 53 of front baseplate 50.

The positions of auxiliary segments 22, 22' in slots 52, 52' are set in monitoring device 1 and cannot be changed from the outside. In this case, fastening arms 55, 55' are secured, for example, by adhesives. In this exemplary embodiment, no auxiliary pointers 26, 26' are necessary. For example, the switch points of switching elements 20, 20' are visualized on scale 2.

Other than the lack of a variable adjustability of the switch points of switching elements 20, 20', the other functions of monitoring device 1 correspond to the exemplary embodiment shown in FIG. 4.

Calibration and adjustment of switching units 200, 200' also occurs in the described manner.

Figure 7:
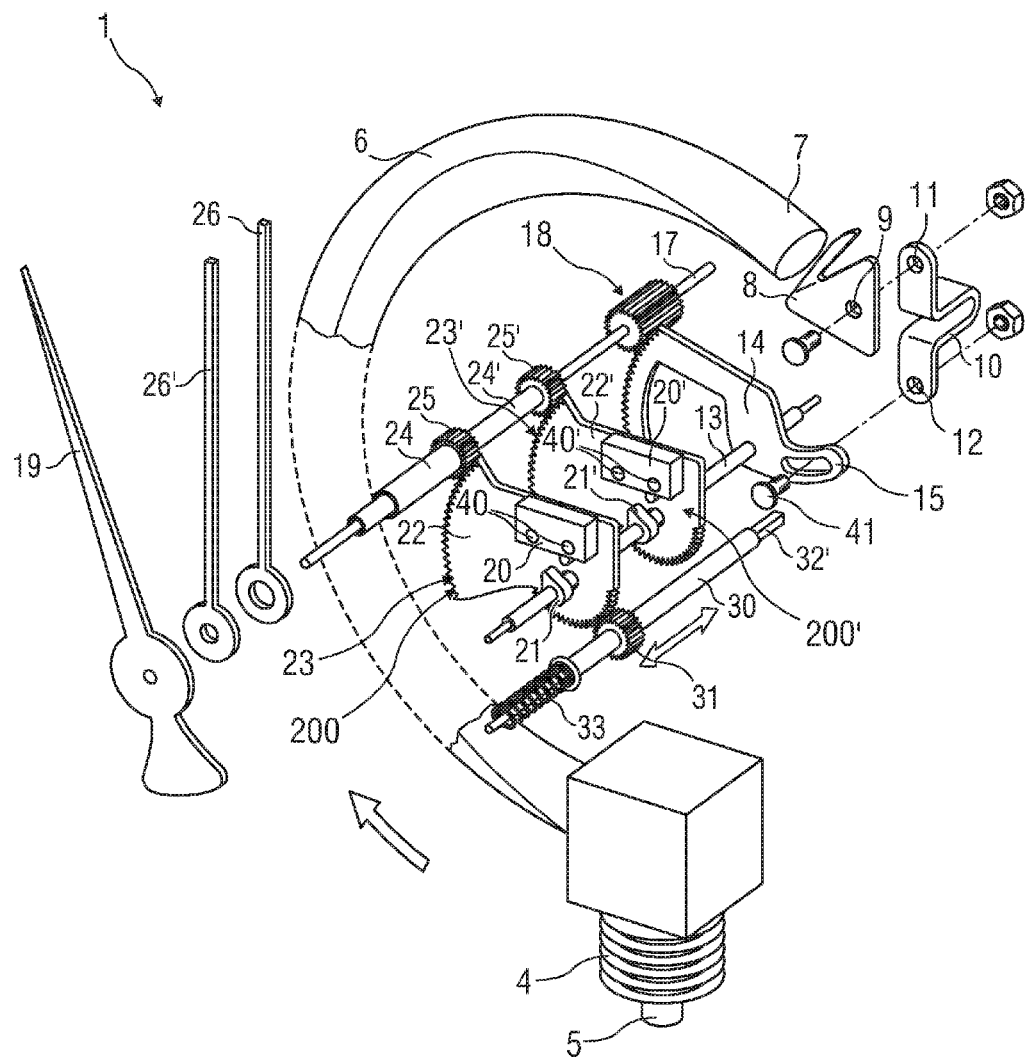
FIG. 7 shows the monitoring device in an exploded view with two identically oriented switching units and auxiliary segments/switch points that can be adjusted from the back.

FIG. 7 shows the monitoring device in an exploded view with two identically oriented switching units and auxiliary segments/switch points that can be adjusted from the back.

The illustrated exemplary embodiment of monitoring device 1 differs from the exemplary embodiment illustrated in FIG. 4 only in that adjustment axis 30 is provided at its back end with a square shaft 32', which can be reached through an opening in the back wall of monitoring device 1.

Figure 8:
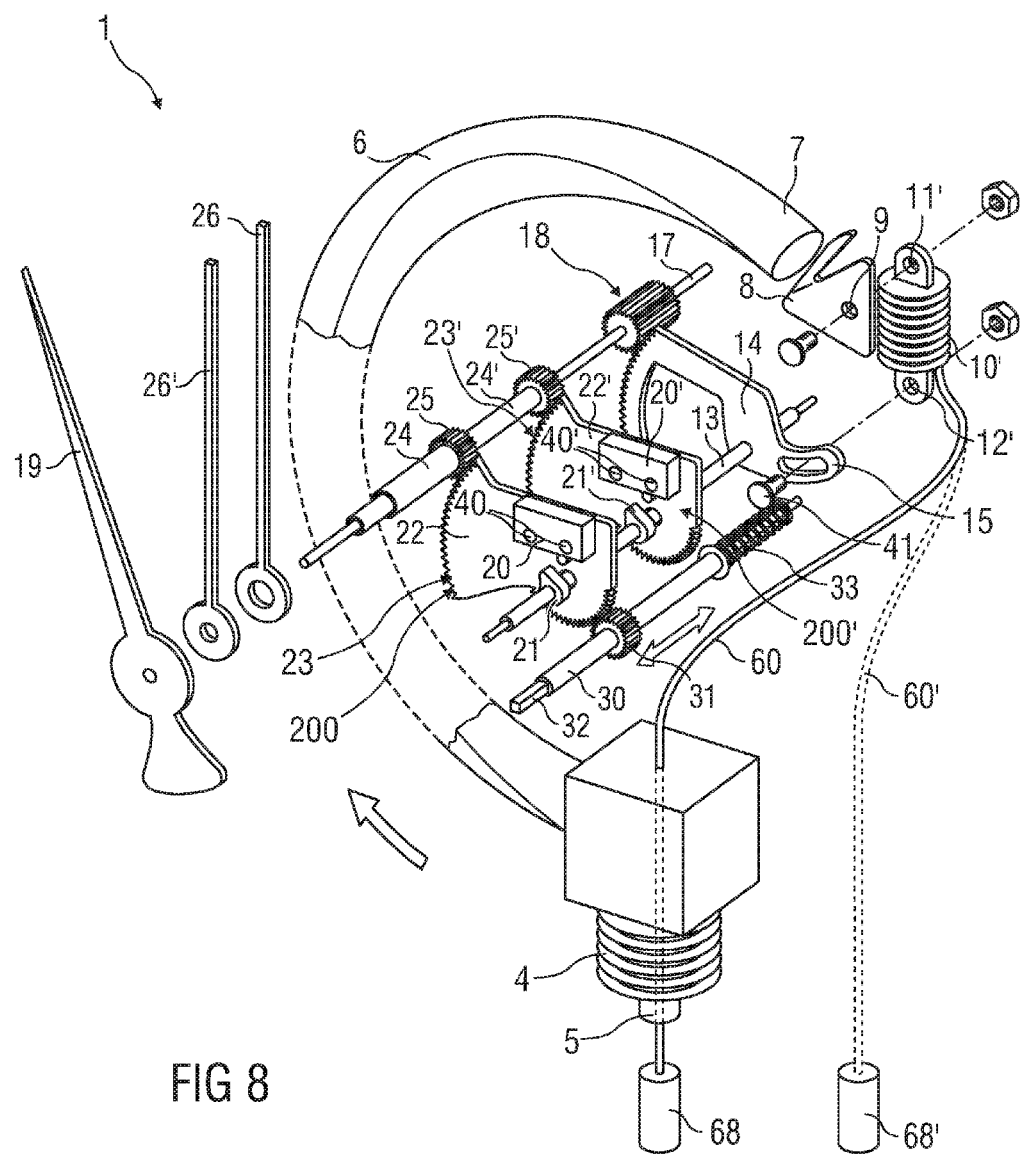
FIG. 8 shows the monitoring device in an exploded view with two identically oriented switching units and bellows as a compensation element.

FIG. 8 shows the monitoring device in an exploded view with two identically oriented switching units and bellows as a compensation element.

The illustrated exemplary embodiment of monitoring device 1 differs from the exemplary embodiment illustrated in FIG. 4 in that a temperature-sensing element 10' is made as a bellows element, which can be aligned and fixed by means of connecting sections 11', 12' between coupling section 8 of pressure-sensing element 6 and the long hole, i.e., the articulation point of articulation section 15 on main segment 14.

The bellows element is filled with a fluid or with a wax, which changes its volume or pressure under the influence of temperature and thus brings about a change in the length of the bellows element.

In particular, for this purpose, a volume accumulator 68 in the application device is placed as part of the monitoring device in the area of pressure connection 5, so that an actually present temperature of the application device can be passed on to temperature-sensing element 10'. To this end, volume accumulator 68 is passed via an elastic capillary 60 through pressure connection 5 pressure-tight to the bellows element in monitoring device 1.

Alternatively, a volume accumulator 68' can also be installed at a different point outside the application device and the temperature information passed via a lengthened capillary 60' into monitoring device 1 to temperature-sensing element 10'.

The other functions, including the calibration and adjustment, of monitoring device 1 correspond to the exemplary embodiment illustrated in FIG. 4.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A monitoring device for a temperature-compensated monitoring of a pressure of a gas or a protective gas in a high-performance switching system, the monitoring device comprising:
    a pressure-sensing element that has a coupling section that is deflectable in response to a gas pressure variation;
    a temperature-sensing element that has a variable length between a first and a second connecting section in response to a temperature variation;
    a main segment rotatable about a main axis with an articulation section attached thereto, the temperature-sensing element with the first connecting section being coupled to the coupling section of the pressure-sensing element and acts with the second connecting section together with the articulation section to influence a rotational position of the main segment about the main axis; and
    at least one first switching unit comprising:
        a first electrical switching element that is actuated by a rotatable cam coupled to the main segment, the cam being rotatable about the main axis; and
        a first auxiliary segment that is rotatable about the main axis and to which the first electrical switching element is attached such that a relative position between the cam and the first electrical switching element is changed by changing the rotational position of the first auxiliary segment,
    wherein the cam and the first auxiliary segment are mounted coaxially on the main axis,
    wherein the first auxiliary segment is adapted to be engaged selectively with an adjustment gearing that is manually rotatable so that by rotating the adjustment gearing, a switch point of the first electrical switching element is adjusted with reference to the rotational position of the cam rotatable with the main segment, and
    wherein the adjustment gearing includes a toothed gear mounted on an adjustment axis that extends essentially parallel to the main axis, wherein teeth of the toothed gear of the adjustment gearing mesh with teeth of the first auxiliary segment.

2. The monitoring device according to claim 1, further comprising a second switching unit comprising:
    a second electrical switching element that is actuated by a rotatable cam coupled to the main segment; and
    a second auxiliary segment that is rotatable about the main axis and to which the second electrical switching element is attached such that a relative position between the cam and the second electrical switching element is changed by changing the rotational position of the second auxiliary segment.

3. The monitoring device according to claim 2, further comprising a third switching unit comprising:
    a third electrical switching element that is actuated by a rotatable cam coupled to the main segment; and
    a third auxiliary segment that is rotatable about the main axis and to which the third electrical switching element is attached such that a relative position between the cam and the third electrical switching element is changed by changing the rotational position of the third auxiliary segment.

4. The monitoring device according to claim 1, wherein the main segment engages in teeth mounted on a main pointer shaft and a rotation of the main segment causes a deflection of a main pointer mounted on the main pointer shaft.

5. The monitoring device according to claim 3, wherein the second auxiliary segment and/or the third auxiliary segment are adapted to be engaged selectively with the adjustment gearing that is manually rotatable so that by rotating the adjustment gearing, a switch point of the second electrical switching element and/or of the third electrical switching element is adjusted with reference to the rotational position of the corresponding cam rotatable with the main segment.

6. The monitoring device according to claim 5, wherein the selective engagement between the rotatable adjustment gearing and the first auxiliary segment and/or the second auxiliary segment and/or the third auxiliary segment is effected by an axial movability of the adjustment gearing, such that the adjustment gearing is axially displaceable along the adjustment axis.

7. The monitoring device according to claim 3, wherein the first auxiliary segment and/or the second auxiliary segment and/or the third auxiliary segment each engage in teeth mounted on an auxiliary pointer shaft and a rotation of the respective auxiliary segment causes a deflection of an auxiliary pointer mounted on the respective auxiliary pointer shaft.

8. The monitoring device according to claim 7, wherein the main pointer shaft and the auxiliary pointer shaft are arranged coaxially to one another.

9. The monitoring device according to claim 1, wherein the temperature-sensing element is a bimetallic element or a bellows element, wherein the bellows element is filled with a wax or a fluid, which acts with a change in response to a temperature variation, and wherein an external volume, coupled pressure-tight to the bellows element, is attached to an application device, in a gas tank, or in an area of the pressure connection of the monitoring device.

10. A high-performance switching system comprising:
at least one electrical switch encapsulated in a protective gas atmosphere, wherein the protective gas atmosphere is set to an allowable pressure and/or density range; and
a monitoring device according to claim 1, which is integrated into the high-performance switching system to detect the pressure and/or the density of the gas, forming the protective gas atmosphere, wherein an exceeding and/or falling below the allowable pressure and/or density range can be output to the outside by electrical signals of at least the first electrical switching element or in addition of a second electrical switching element and/or of a third electrical switching element of the monitoring device.

11. The high-performance switching system according to claim 10,
wherein the monitoring device emits an electrical signal when the pressure and/or the density of the protective gas atmosphere has approached a top or bottom limit of the allowable pressure and/or density range at a predefined distance, or
wherein when the monitoring device detects that the predefined pressure and/or density range has been left, an alarm is generated and/or switching processes in the high-performance switching system are prevented, and a warning notification is generated if it is detected that the pressure and/or density of the protective gas atmosphere has approached the top or bottom limit of the allowable pressure and/or density range at a predefined distance.

12. The high-performance switching system according to claim 10, wherein when the monitoring device detects that the predefined pressure and/or density range has been left, an alarm is generated and/or switching processes in the high-performance switching system are prevented, and a warning notification is generated if it is detected that the pressure and/or density of the protective gas atmosphere has approached a top or bottom limit of the allowable pressure and/or density range at a predefined distance.

13. The monitoring device according to claim 5, wherein teeth of the toothed gear of the adjustment gearing mesh with teeth of the second auxiliary segment and/or teeth of the third auxiliary segment.

* * * * *